United States Patent [19]

Langton

[11] Patent Number: 5,649,538

[45] Date of Patent: Jul. 22, 1997

[54] SIMULATION OF BONE IN ULTRASONIC ASSESSMENT APPARATUS

[75] Inventor: Christian McDonald Langton, Hull, Great Britain

[73] Assignee: McCue PLC, London, England

[21] Appl. No.: 599,338

[22] Filed: Feb. 8, 1996

[30]  Foreign Application Priority Data

Feb. 8, 1995 [GB] United Kingdom ............. 9502448

[51] Int. Cl.⁶ ............................................. A61B 8/00
[52] U.S. Cl. .......................................... 128/661.03
[58] Field of Search .................. 128/660.01, 660.02, 128/660.03, 660.06, 661.03, 662.03

[56]  References Cited

U.S. PATENT DOCUMENTS 3,847,141  11/1974  Hoop .
4,016,750  4/1977   Green .
5,143,069  9/1992   Kwon .
5,535,750  7/1996   Matsui et al. ................. 128/661.03

OTHER PUBLICATIONS

Ching et al, "Resolution Enhancement in Ultrasonic Imaging By a Time–Varying Filter", SPIE vol. 768 International Symposium on Pattern Recognition and Acoustical Imaging (1987), pp. 79–84 [XP 000569259].

Primary Examiner—George Manuel
Attorney, Agent, or Firm—Cushman Darby & Cushman IP Group of Pillsbury Madision & Sutro, LLP

[57]  ABSTRACT

A simulation device for simulating bone in an ultrasonic assessment apparatus comprises an electrical low-pass filter (20). The filter (20) attenuates the ultrasonic signal of the apparatus to simulate the attenuating effect of bone on the signal transmitted by a transmitting transducer (1) of the apparatus.

21 Claims, 4 Drawing Sheets

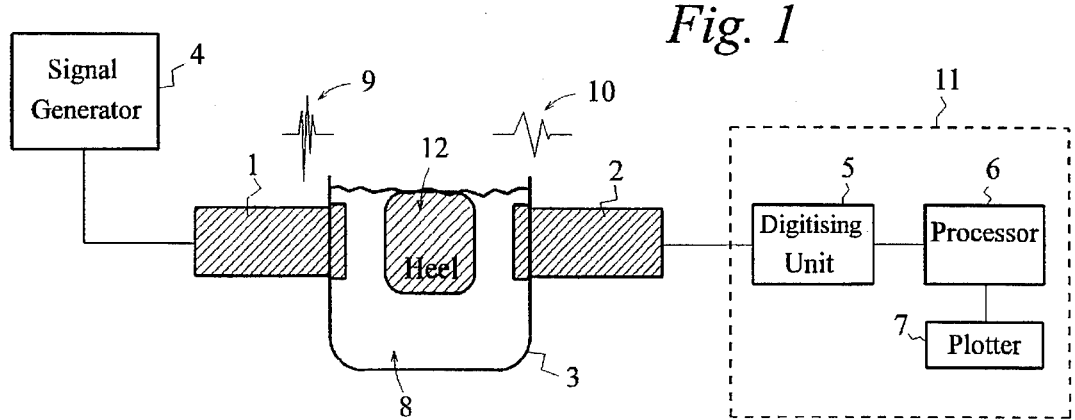
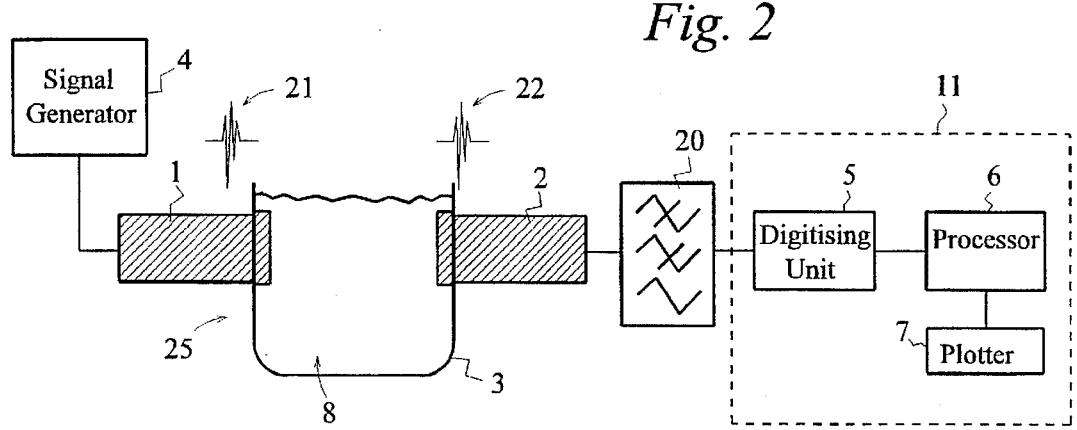
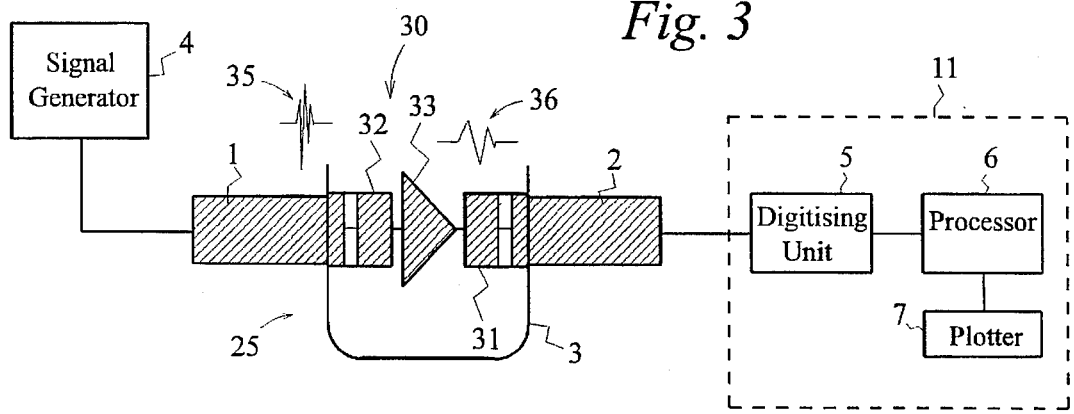

5,649,538

SIMULATION OF BONE IN ULTRASONIC ASSESSMENT APPARATUS

FIELD OF THE INVENTION

This invention relates to a simulation device, to a method for simulating bone in an ultrasonic assessment apparatus, and to such an apparatus.

BACKGROUND ART

There is an increasing interest in the use of ultrasonic velocity and attenuation (Broadband Ultrasonic Attenuation, BUA) measurements in human bone, particularly the human calcaneum (heel) to identify and monitor osteoporotic changes.

A known ultrasonic assessment apparatus is illustrated diagrammatically in FIG. 1 of the accompanying drawings. The apparatus comprises a primary ultrasonic transmitting transducer 1, a primary ultrasonic receiving transducer 2 and a vessel 3 containing a suitable liquid 8, typically water, through which the transmitted ultrasonic signal 9 can propagate.

An electrical signal generator 4 is connected to supply a short voltage pulse e.g. 600 V, 1 μs, to the input of the transmitting transducer 1. The output 10 from the receiving transducer is fed to an analyser 11 comprising a digitising unit 5 and a processor 6 programmed to perform a Fast Fourier Transform (FFT) on the digitised data. The processor 6 is also programmed to analyse the resultant frequency spectrum to produce a plot of attenuation as a function of frequency which may then be printed out using a plotter 7 or the like.

The slope of the attenuation/frequency plot expressed in $dBMHz^{-1}$ is known as the BUA value and provides an indication of bone condition.

In use, the patient's heel 12 is placed in the vessel 3, as shown, the equipment operates and the frequency spectrum is measured. In this way, the attenuation of the transmitted ultrasonic pulse due to absorption by the patient's heel 12 can be measured over a desired frequency range. Typically, measurements are made over the frequency range from 0.2 MHz to 0.6 MHz. For the human heel, the slope of a plot of attenuation against frequency may lie in a range from about 20 $dBMHz^{-1}$ (a BUA value of 20) to 120 $dBMHz^{-1}$ (a BUA value of 120), depending on bone condition, with a typical attenuation of about 10 dB at 0.2 MHz.

In an alternative, "dry", design of ultrasonic assessment apparatus as shown in the applicants prior U.S. Pat. No. 5,452,722 (the contents of which are incorporated herein by reference), the ultrasonic transmitting and receiving transducers 1, 2 are positioned directly against the patient's heel using soft coupling pads to accommodate variations of heel shape.

In order to compensate for any frequency dependency of the transducer response the frequency spectra obtained are initially corrected by subtracting a reference spectrum derived from a reference material, such as de-gassed water. In the case of an assessment apparatus comprising a water-filled vessel, the reference spectrum may be updated regularly.

In order to monitor the reliability and repeatability of the measurements it is necessary to provide a standard (a so-called quality assurance phantom) which simulates the attenuation properties of bone.

However, such quality assurance phantoms tend to be unreliable, especially when they are used to simulate the attenuating effect of cancellous bone. Furthermore it is very difficult to accurately simulate bone properties using a physical substitute.

Epoxy-resin models of CAD heel structures have been produced using stereo-lithography techniques. Models produced in this way have a highly repeatable structure; nevertheless, they are found to exhibit an inter and intra phantom precision (i.e. a coefficient of variation) of about 4%, a value which is considered to be too high.

In an alternative design, bone structure is simulated in a model by gelatine pellets randomly dispersed in epoxy resin. However, this design has the drawback that there is very little control over the internal structure of the model.

SUMMARY OF THE INVENTION

Whereas the aforementioned designs rely upon structural means to simulate the ultrasonic attenuation properties of bone, the present invention, in contrast, uses electrical means.

According to one aspect of the invention there is provided a simulation device for simulating bone in an ultrasonic assessment apparatus, the simulation device including electrical means (e.g. filter means) for simulating the attenuating effect of bone on an ultrasonic signal transmitted by the ultrasonic assessment apparatus.

For the avoidance of doubt, the term "electrical" includes "electronic" apparatus.

A simulation device according to the invention has the advantage that the simulated attenuation is determined by the electrical properties of the electrical filter means, and is not dependent on factors such as the physical structure and composition of a model which, as already explained, may reduce the accuracy of the measurements being made.

The ultrasonic signal, or an electrical signal indicative of or relating to the ultrasonic signal, is preferably passed through the electrical or electronic means, where the signal's character, properties or form are altered by the electrical or electronic means in a similar or identical way to the way in which they would have been altered had the signal passed through a particular bone or bone structure.

The electrical properties of the electrical means preferably mimic the attenuating properties of the particular bone structure being simulated. In other words, the assessment apparatus may produce the same response when the simulation device is being used as it would if the particular bone being simulated was in place in the assessment apparatus.

The filter means may be a band-pass filter and is preferably a low-pass filter. It may have a frequency response tailored to simulate the attenuating effect of a chosen bone condition.

The filter means may have a fixed frequency response to simulate the attenuating effect of a particular bone condition. In this case, the filter means may be a low pass filter having a predetermined slope in the roll-off region of the frequency response.

Alternatively, the filter means may have an adjustable frequency response so as to be capable of simulating the attenuating effects of a range of different bones and/or bone conditions. In other words the simulation device may include adjustment means for adjusting the performance of the filter means such that the filter means may simulate different attenuation effects. In this case, the electrical filter means may be a band or low-pass filter having an adjustable slope in the roll-off region of the frequency response.

The electrical filter means may have an input, an output, a plurality of filter stages and adjustable means (e.g. switch means) for selectively connecting one, and/or an arrangement (e.g. serial) of two or more, of said filter stages between the input and the output whereby to adjust the frequency response of the filter means. The filter stages may all have the same frequency response. In this way, an operator may calibrate or check the ultrasonic assessment apparatus for a number of different bones and/or bone conditions.

The electrical filter means may have a slope in the roll-off region of the frequency response which is adjustable over a predetermined range e.g. from about 20 dBMHz$^{-1}$ to about 120 dBMHz$^{-1}$.

The simulation device may also include means for delaying a received signal. The delay means may take the form of an electrical delay line, and the delay line may provide an adjustable delay in order to simulate different propagation velocities of an ultrasonic signal through bone.

Typically the ultrasonic assessment apparatus includes a primary ultrasonic transmitting transducer and a primary ultrasonic receiving transducer.

In one preferred embodiment of the invention, the simulation device is connectable to the output of the ultrasonic receiving transducer. In this case, the receiving transducer receives the transmitted ultrasonic signal and the simulation device attenuates the received signal in order to simulate the attenuating effect of bone on the transmitted ultrasonic signal.

In another preferred embodiment of the invention, the simulation device is placed between the transmitting and receiving transducers of the ultrasonic assessment apparatus in the position normally occupied by a bone under test. In this embodiment, the simulation device comprises secondary ultrasonic receiving and transmitting transducers for respectively receiving an ultrasonic signal from and transmitting an ultrasonic signal to the transmitting and receiving transducers of the ultrasonic assessment apparatus, and the electrical filter means is connected between the secondary receiving and transmitting transducers of the simulation device, whereby to simulate the attenuating effect of bone on the ultrasonic signal transmitted by the transmitting transducer of the ultrasonic assessment apparatus.

The aforementioned delay could alternatively be implemented by means of a physical delay in the form of a low velocity material (for example silicone rubber) attached to one or both of the secondary transducers.

The filter means may be implemented in any suitable manner, e.g. using analogue or digital circuitry or a computer controlled filter, or any combination of these as appropriate.

The character of the primary ultrasonic transmitting and/or receiving transducers may vary depending on the particular ultrasonic assessment apparatus in question. In particular the transducers may be either of the focused or unfocused type. The secondary transducers may therefore be chosen to complement the primary transducers of the assessment apparatus, and in some embodiments the secondary transducers may be removable and/or interchangeable to allow different secondary transducers to be used with different types of ultrasonic assessment apparatus.

In accordance with a further aspect of the invention there is provided a method for simulating bone in an ultrasonic assessment apparatus, the method including using electrical or electronic means (e.g. filter means) to simulate the attenuating effect of bone on an ultrasonic signal transmitted by the ultrasonic assessment apparatus.

According to a yet further aspect of the invention there is provided an ultrasonic assessment apparatus incorporating a simulation device as defined herein in accordance with the present invention. The assessment apparatus may include ultrasonic transmitting and receiving transducers and, possibly, means for locating the transducers against or adjacent a patient's body part e.g. heel. The assessment apparatus may be adapted for ultrasonic assessment of any particular bone and may include means for locating the body part containing that bone in the desired position on the apparatus.

The invention also provides for use of electrical or electronic filter means for simulating bone in an ultrasonic assessment apparatus.

BRIEF DESCRIPTION OF THE DRAWINGS

Embodiments of the invention are now described, by way of example only, with reference to the accompanying drawings, in which:

FIG. 1 illustrates diagrammatically a known ultrasonic assessment apparatus;

FIG. 2 shows a simulation device according to an embodiment of the invention;

FIG. 3 shows a simulation device according to a second embodiment of the invention;

DETAILED DESCRIPTION OF THE EMBODIMENTS

Figure 4:
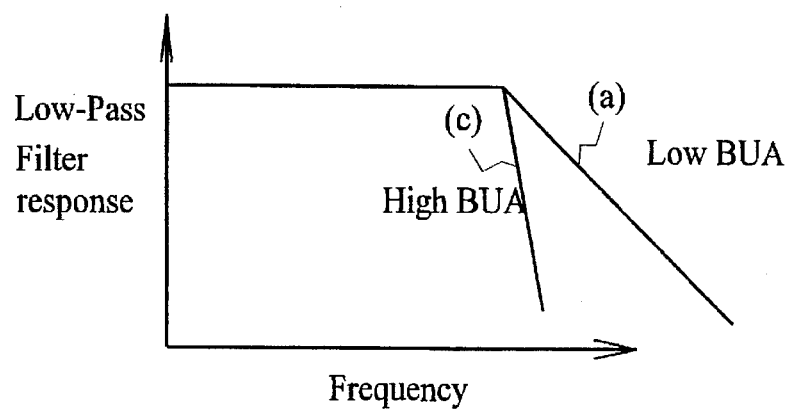
FIG. 4 illustrates the frequency responses of two low-pass filters simulating high and low BUA values.

Referring to FIG. 2, the simulation device comprises a low-pass filter 20 connected to the output of the ultrasonic receiving transducer 2 of the ultrasonic assessment apparatus (generally indicated 25).

The transmitted ultrasonic signal 21 propagates through e.g. water 8 contained in vessel 3 of the apparatus and the received signal 22 is directly received by the receiving transducer 2.

The low-pass filter 20 attenuates the output signal from the receiving transducer 2 (corresponding to signal 22) in order to simulate the attenuating effect of bone on the ultrasonic signal 21 transmitted by the transmitting transducer 1. The signal is then processed by analyser 11.

In the embodiment shown in FIG. 3, the simulation device 30 (shown schematically) is placed within vessel 3 between the transmitting and receiving transducers 1, 2 of the ultrasonic assessment apparatus.

The device 30 comprises secondary ultrasonic transmitting and receiving transducers 31, 32 and circuitry 33 interconnecting the secondary transducers. Circuitry 33 includes a filter (e.g. low-pass) and may also include an amplifier and/or delay circuitry.

The secondary transducers may contact the respective primary transducers (as shown) or alternatively may be coupled to the transducers using an intermediary material, or even a fluid such as water (as in FIG. 2).

The secondary receiving transducer 32 receives an ultrasonic signal 35 transmitted by transducer 1, and the low-pass filter in circuitry 33 attenuates the output signal from the secondary receiving transducer 32. The attenuated signal 36 is then transmitted by the secondary transmitting transducer 31 and is received by the receiving transducer 2 of the assessment apparatus.

An amplifier, typically having a gain of about 50 dB, may be provided to compensate for transfer attenuation caused by the use of the secondary transducers 31, 32.

As in the case of the simulation device described with reference to FIG. 2, the low-pass filter in circuitry 33 is effective to simulate the attenuating effect of bone on the ultrasonic signal transmitted by the transmitting transducer 1. To this end, the frequency responses of the low-pass filters 20, 33 are tailored to simulate a desired attenuating effect.

Curve (a) in FIG. 4 illustrates the frequency response of a low-pass filter suitable for simulating bone having a relatively low attenuating effect. In this case, the slope in the roll-off region of the frequency response may typically be in the region of 20 dBMHz$^{-1}$, simulating a low BUA value (i.e. 20).

By way of contrast, curve (c) in FIG. 4 illustrates the frequency response of a low-pass filter suitable for simulating bone having a relatively high attenuating effect. In this case, the slope in the roll-off region of the frequency response may typically be in the region of 100 dBMHz$^{-1}$, simulating a high BUA value (i.e. 100). Curves (a) and (c) correspond to the lines (a) and (c) respectively in the graph of FIG. 6.

In general, the design of the electrical filter will be optimised to give a required frequency response commensurate with the attenuating effect of a chosen bone or bone condition.

Figure 5:
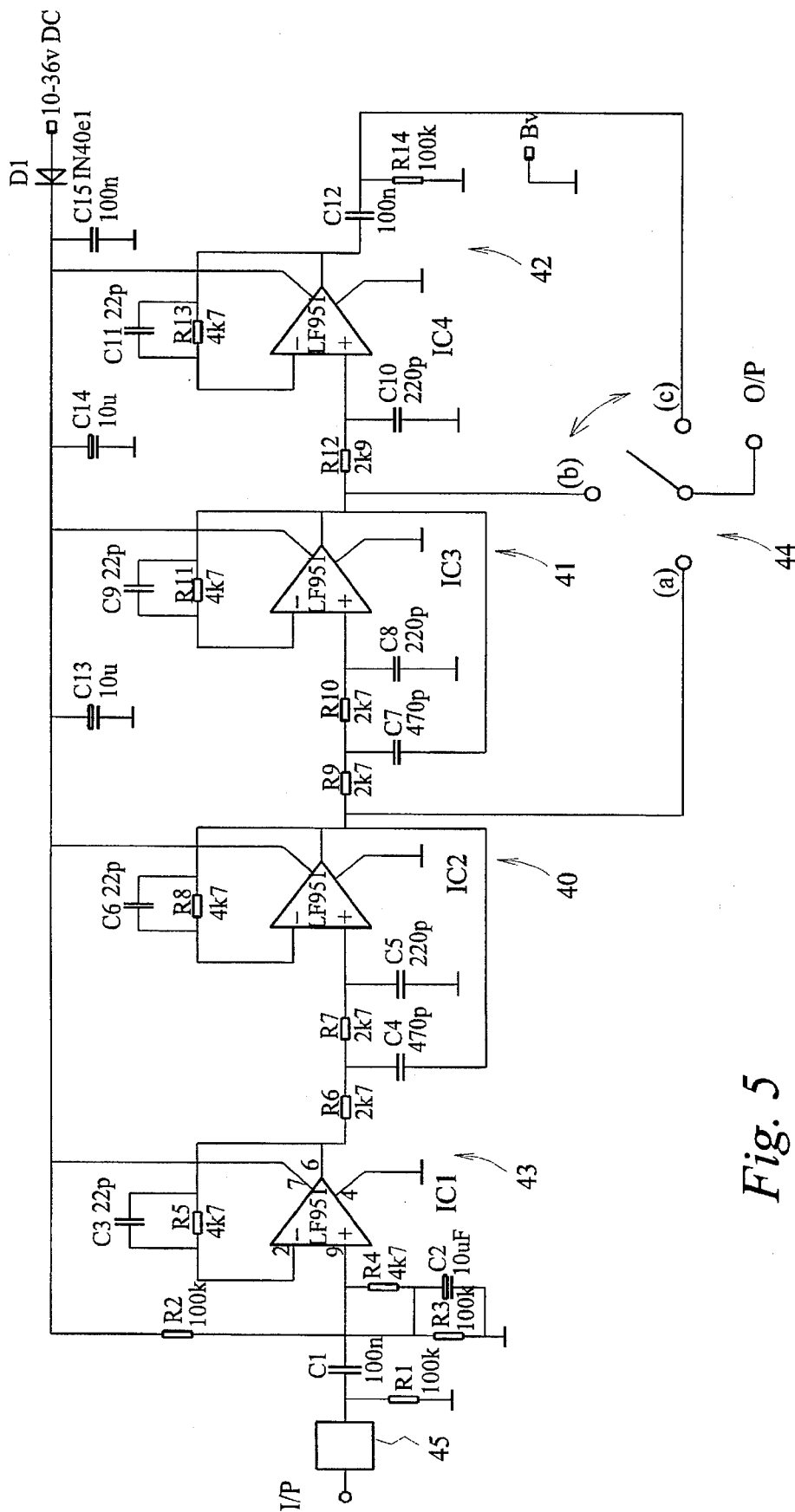
FIG. 5 shows a circuit diagram of an analogue simulation device according to the invention.

FIG. 5 shows, by way of example, a simulation device comprising three, serially-connected, filter stages 40, 41, 42. The first filter stage 40 is connected to the device input (I/P) via a buffer stage 43 which keeps the source impedance to the filter stages low—at about 4.5 KΩ in this embodiment.

Filter stages 40 and 41 are second-order filter stages, whereas filter stage 42 is a single order stage. Each stage could be of any order required. In this embodiment, the filter stages are designed so that each order has a slope in the roll-off region of the frequency response of about 20 dBMHz$^{-1}$, giving an overall slope of about 100 dBMHz$^{-1}$. It will be appreciated that the simulation device could have fewer than or more than three filter stages, and fewer than or more than five orders.

In order to minimize passband ripple, the Q of each filter stage is set at about 0.7, giving a gradual roll-off extending well into the passband.

In order to simulate the broadband ultrasonic attenuation of bone, the turnover frequency of each filter stage is preferably set at about 0.2 MHz, the lowest frequency at which bone begins to have a significant attenuating effect on ultrasound. In this particular embodiment, the actual turnover frequencies of the first and second order filter stages are 0.185 MHZ and 0.183 MHZ respectively, so that, like bone, the level of attenuation will be about 10 dB at 0.2 MHz.

Figure 6:
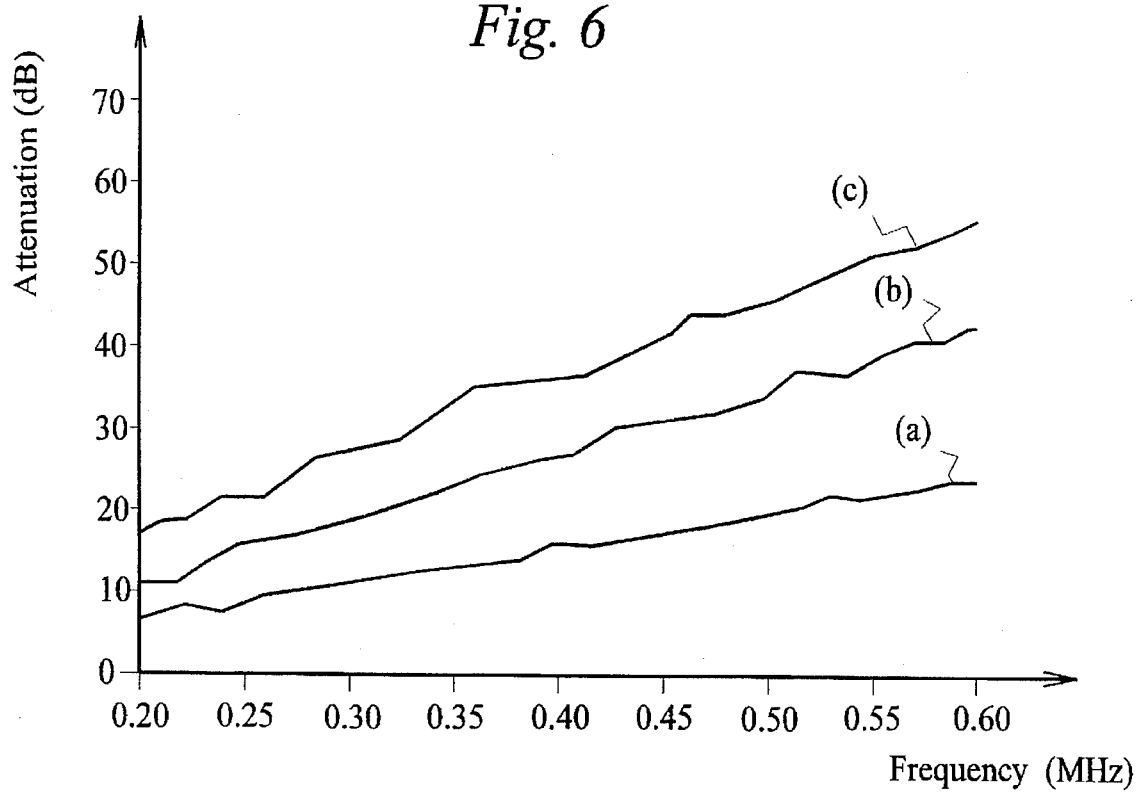
FIG. 6 shows different plots of attenuation as a function of frequency derived using the simulation device of FIG. 5.

In this embodiment, the filter has an adjustable control 44 for selectively connecting a desired number of the stages between the device input (I/P) and the device output (O/P). Thus, if only the first stage 40 is selected (giving two orders) the resultant slope in the roll-off region of the frequency response will be about 40 dBMHz$^{-1}$, if the first and second stages 40, 41 are selected (giving four orders) the resultant slope will be about 80 dBMHz$^{-1}$, whereas if all three stages 40, 41, 42 are selected (giving five orders) the resultant slope will be about 100 dBMZ$^{-1}$. FIG. 6 shows actual plots of attenuation as a function of frequency in the roll-off region derived using the simulation device described with reference to FIG. 5.

The terminals of the adjustable control 44 are labelled a, b and c. These terminals correspond to the three lines a, b, and c on the graph of FIG. 6. In other words if the adjustable control 44 is set to position a then the attenuation response of line a in FIG. 6 will be achieved. Similarly for terminals b and c.

A simulation device incorporating an adjustable filter of the kind described is beneficial in that a single device has the capability to simulate the different attenuating effects produced by a range of different bone conditions—hitherto, it has been necessary to simulate different bone conditions using different phantoms.

The velocity of ultrasound through bone is typically in the range from 1475 to 1675 msec$^{-1}$. However, when the simulation device is in use the propagation speed will be much higher. A delay line 45 may be included in order to compensate for this difference. In this way, the assessment apparatus will respond to a simulated input signal as though it were a genuine signal.

The propagation speed through bone is dependent upon bone condition. Accordingly, the simulation device may have an adjustable delay line giving the device the capability to simulate a range of different velocities of ultrasound in bone as well as a range of different attenuation levels.

Figure 7:
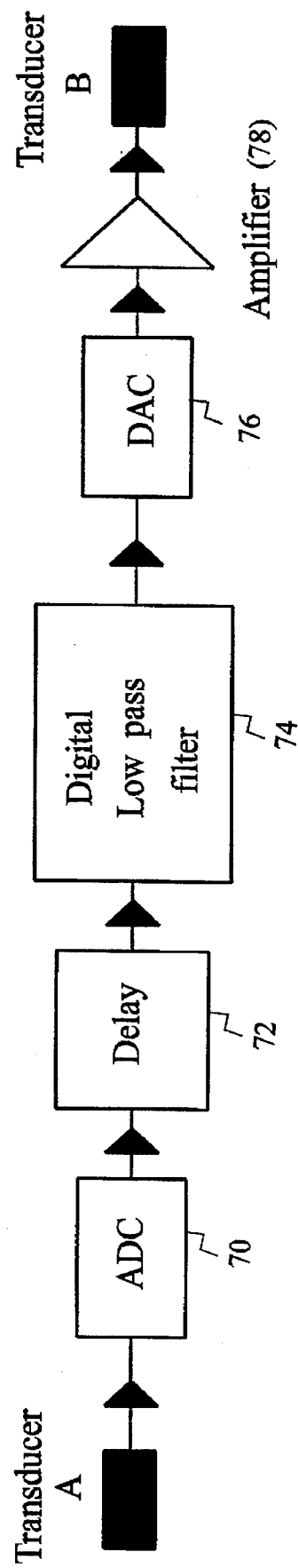
FIG. 7 shows a schematic diagram of a digital simulation device according to the invention.

FIG. 7 shows a schematic diagram of a digital implementation of a simulation device according to the present invention. An analogue implementation (such as that shown in FIG. 5) may lead to problems with one or more of: flexibility, size, accuracy or available delay. By implementing the simulation device using digital components some or all of these problems may be eliminated.

In the embodiment of FIG. 7 the digital electronic phantom consists of a receiving transducer (A) which transmits a received signal to an analogue to digital converter (ADC) (70). The ADC is connected to a digital delay circuit (72) which is usable to slow the signal down to the speed associated with an ultrasound signal. The signal is then passed to a digital low pass filter (74) which simulates the operation of the ultrasound signal passing through a bone. The resulting signal is then passed through a digital analogue converter (DAC) (76) and amplified using amplifier (78). Finally, the signal is output using receiving transducer B.

The digital embodiment of FIG. 7 corresponds broadly to the analogue embodiment of FIG. 3, in that the phantom is located between the transducers of the ultrasonic assessment apparatus and includes a pair of secondary transducers. Alternatively, a digital embodiment may be devised which corresponds to the analogue embodiment of FIG. 2 i.e. where the necessary circuitry is located after the receiving transducer of the ultrasonic assessment apparatus.

The low pass filter may be implemented using an appropriate digital software program and the entire device (including the ADC, low pass filter, delay and DAC) may be implemented using a microprocessor.

Preferably the simulation device should provide the following characteristics:

Ultrasonic signal of approximately 4 μsec is produced by a voltage pulse of 600 V with a width of 1 μsec.

Measurements are to be recorded over a frequency range of 0.2 to 0.6 MHZ.

Simulate attenuation characteristics of bone ranging from 20 to 120 dBMHz$^{-1}$.

The cut off frequency is to be assumed to be 0.18 MHz.

The phantom produces a constant attenuation of 10 dB at 0.2 MHZ.

A delay of 25 μsec is implemented to simulate the propagation of ultrasound through bone.

The phantom provides reproducibility and precision.

An appropriate filter of any type may be designed, but in one embodiment a third order digital Butterworth low pass filter was designed with a cut off frequency of 0.18 MHZ. It has a third order real zero at z=−1 a first order real pole with a radius 0.22353 and angle 0° and a second order complex conjugate pair with radius 0.61402 and angle ±61.48°. This gave a recurrence formula of:

$$y[n]=1.22804 \cos(61.48°)y[n-1]-(0.61402)^2 y[n-2]+v[n]+2v[n-1]+v[n-2]$$

where, $v(n)=0.22353v[n-1]+x[n]+x[n-1]$

The above embodiments of the present invention have been described by way of example only and various alternative features or modifications from what has been specifically described and illustrated can be made within the scope of the invention, as will be readily apparent to a person skilled in the art.

I claim:

1. A simulation device for simulating bone in an ultrasonic assessment apparatus, the simulation device including
an electrical filter for simulating an attenuating effect of bone on an ultrasonic signal transmitted by the ultrasonic assessment apparatus, by altering an ultrasonic signal produced by the ultrasonic assessment apparatus, or an electrical signal indicative of or relating thereto such that a character, property or form of the ultrasonic signal or the electrical signal is altered by the electrical filter in a similar way or an identical way to a way in which the ultrasonic signal or the electrical signal would have been altered had the ultrasonic signal or the electrical signal passed through.

2. The simulation device according to claim 1 wherein the electrical filter is a low-pass filter.

3. The simulation device according to claim 2 wherein the electrical filter has a fixed frequency response having a predetermined slope in a roll-off region of the frequency response to simulate an attenuating effect of a particular bone condition.

4. The simulation device according to claim 2 wherein the electrical filter includes adjustment means for adjusting characteristics of the electrical filter such that the electrical filter is operable to simulate different attenuation effects of a range of at least one of different bones and different bone conditions.

5. The simulation device according to claim 4 wherein the adjustment means is usable to adjust a slope in a roll-off region of a frequency response of the electrical filter.

6. The simulation device according to claim 1 further including delaying means, electrically connected to the electrical filter, for delaying a received signal.

7. The simulation device according to claim 6 wherein the delaying means is an electrical delay line which is operable to provide an adjustable delay in order to simulate different propagation velocities of the ultrasonic signal through bone.

8. The simulation device according to claim 1 further comprising means for connecting the simulation device to an output of an ultrasonic receiving transducer of the ultrasonic assessment apparatus.

9. The simulation device according to claim 1, wherein the simulation device is implemented using a microprocessor.

10. A simulation device for simulating bone in an ultrasonic assessment apparatus, the simulation device comprising an electrical filter for simulating an attenuating effect of bone on an ultrasonic signal transmitted by the ultrasonic assessment apparatus, wherein the simulation device is locatable between a primary transmitting transducer and a primary receiving transducer of the ultrasonic assessment apparatus in a position normally occupied by a bone under test, and the simulation device includes a secondary ultrasonic receiving transducer and a secondary ultrasonic transmitting transducer for respectively receiving the ultrasonic signal from and transmitting the ultrasonic signal to the primary transmitting transducer and the primary receiving transducer of the ultrasonic assessment apparatus respectively, and the electrical filter is connected between the secondary ultrasonic receiving transducer and the secondary ultrasonic transmitting transducer of the simulation device.

11. The simulation device according to claim 10 wherein the secondary ultrasonic transmitting transducer and the secondary ultrasonic receiving transducer are removable to allow different secondary transducers to be used with different types of ultrasonic assessment apparatus.

12. The simulation device according to 10, further comprising
delay means, for delaying a received signal, attached to at least one of the secondary ultrasonic transmitting transducer and the secondary ultrasonic receiving transducer.

13. The simulation device according to claim 12, wherein the delay means is a low velocity material.

14. The simulation device according to claim 12, wherein the delay means is silicone rubber.

15. An ultrasonic assessment apparatus incorporating a simulation device for simulating bone in an ultrasonic assessment apparatus, the simulation device including
an electrical filter for simulating an attenuating effect of bone on an ultrasonic signal transmitted by the ultrasonic assessment apparatus, by altering an ultrasonic signal produced by the ultrasonic assessment apparatus, or an electrical signal indicative of or relating thereto such that a character, property or form of the ultrasonic signal or the electrical signal is altered by the electrical filter in a similar or identical way to a way in which the ultrasonic signal or the electrical signal would have been altered had the ultrasonic signal or the electrical signal passed through.

16. A simulation device for simulating bone in an ultrasonic assessment apparatus, the simulation device including:
an electrical low pass filter and delay means for simulating an attenuating effect of the bone on an ultrasonic signal transmitted by the ultrasonic assessment apparatus wherein in use an ultrasonic signal produced by the ultrasonic assessment apparatus, or an electrical signal indicative of or relating to the ultrasonic signal, is passed through the electrical filter such that a character, a property or a form of the ultrasonic signal or the electrical signal is altered by the electrical low pass filter in a similar way or an identical way to a way in which the ultrasonic signal or the electrical signal would have been altered had the ultrasonic signal or the electrical signal passed through a particular bone or a bone structure, wherein the electrical low pass filter has a fixed frequency response having a predetermined slope in a roll-off region of the frequency response to simulate an attenuating effect of a particular bone condition, and the electrical low pass filter includes adjustment means for adjusting the predetermined slope in the roll-off region of the frequency response of the electrical low pass filter means such that the electrical low pass filter is operable to simulate different attenuation effects of a range of at least one of different bones and different bone conditions.

17. A method for simulating bone in an ultrasonic assessment apparatus, comprising steps of:

producing an ultrasonic signal by the ultrasonic assessment apparatus;

passing the ultrasonic signal or an electrical signal indicative of the ultrasonic signal through an electrical filter; and altering characteristics of the ultrasonic signal or the electrical signal by the electrical filter in a similar way or an identical way to a way in which the ultrasonic signal or the electrical signal would have been altered had the ultrasonic signal or the electrical signal passed through a particular bone or a bone structure.

18. A simulation device for simulating bone in an ultrasonic assessment apparatus, the simulation device comprising:

an electrical filter for simulating an attenuating effect of bone on an ultrasonic signal transmitted by the ultrasonic assessment apparatus; and delaying means, electrically connected to the electrical filter means, for delaying a received signal.

19. The simulation device according to claim 18, wherein the delaying means is an electrical delay line.

20. The simulation device according to claim 19, wherein the electrical delay line includes an adjustable delaying means for adjusting a delay time.

21. A simulation device for simulating bone in an ultrasonic assessment apparatus, the simulation device comprising:

an analog to digital converter to convert a received signal to a digital signal;

a first receiving transducer, electrically connected to the analog to digital converter, which transmits the received signal to the analog to digital converter;

a digital delay circuit electrically connected to the analog to digital converter for receiving the digital signal from the analog to digital converter and slowing down the digital signal to a speed associated with an ultrasound signal;

a digital low pass filter electrically connected to the digital delay circuit to receive the digital signal from the digital delay circuit and alter the digital signal so as to simulate an operation of the ultrasound signal passing through a bone;

a digital to analog converter, electrically connected to the digital low pass filter, to receive the digital signal altered by the digital low pass filter and convert the digital signal to an analog signal;

an amplifier, electrically connected to the digital to analog converter, to receive the analog signal from the analog to digital converter and to output an amplified analog signal; and a second receiving transducer, electrically connected to the amplifier, to receive the amplified analog signal and to output a corresponding signal.

* * * * *